United States Patent [19]

Laforest, nee Boutillier du Retail et al.

[11] 4,195,093
[45] Mar. 25, 1980

[54] FUROYL- AND THENOYL-ARYLOXYALKYL CARBOXYLIC ACID DERIVATIVES, THEIR PREPARATION AND THEIR USE IN THERAPY

[75] Inventors: Jacqueline S. Laforest, nee Boutillier du Retail, Vincennes; Sylviane S. J. Mignonac, nee Mondon, Chilly-Mazarin; Germaine Thuillier, nee Nachmias, Paris; Pierre A. R. Bessin, Chilly-Mazarin, all of France

[73] Assignee: Albert Rolland S.A., Paris, France

[21] Appl. No.: 889,986

[22] Filed: Mar. 24, 1978

[30] Foreign Application Priority Data

Apr. 6, 1977 [FR] France .................................. 77 10405

[51] Int. Cl.² .................... A61K 31/38; A61K 31/34; C07D 333/24; C07D 307/77
[52] U.S. Cl. .................................. 424/275; 424/285; 260/346.22; 260/346.73; 260/347.3; 549/49; 549/58; 549/74; 549/75; 549/77; 549/78; 549/79
[58] Field of Search .................. 260/332.2 A, 347.3, 260/330.5, 346.22, 346.73; 424/275, 285

[56] References Cited

U.S. PATENT DOCUMENTS 3,758,506  9/1973  Godfroid et al. ............. 260/332.2 A

OTHER PUBLICATIONS

Weininger, "Contemporary Org. Chem.", p. 260 (1972).

Primary Examiner—Alan Siegel
Attorney, Agent, or Firm—Stevens, Davis, Miller & Mosher

[57] ABSTRACT

Compounds of the general formula I

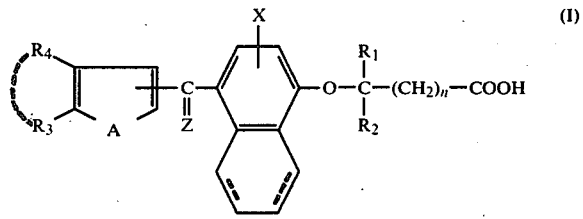

wherein n represents 0, 1 or 2, A represents oxygen or sulphur, Z represents oxygen or hydroxyimino, X represents hydrogen, or halogen, the dotted lines represent bonds which may be unsaturated or saturated, $R_1$ and $R_2$ each represent hydrogen or alkyl, and $R_3$ represents hydrogen, halogen or methyl, and $R_4$ represents a hydrogen atom, or $R_3$ and $R_4$ together with the two carbon atoms to which they are attached represent benzene, and their pharmaceutically acceptable salts are useful in therapy, in particular as uricosuric agents or as diuretic and uricosuric agents.

10 Claims, No Drawings

FUROYL- AND THENOYL-ARYLOXYALKYL CARBOXYLIC ACID DERIVATIVES, THEIR PREPARATION AND THEIR USE IN THERAPY

The present invention relates to furoyl- and thenoylaryloxyalkyl carboxylic acid derivatives and their pharmaceutically acceptable salts, as well as to their preparation and their use in therapy, in particular as uricosuric or uricosuric and diuretic agents.

According to the present invention, there are provided compounds of the general formula I

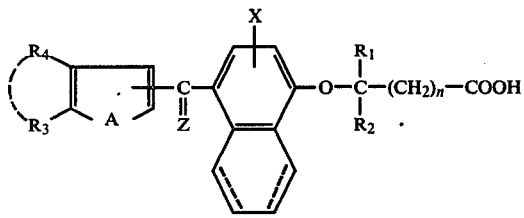

(I)

wherein
n represents 0, 1 and 2,
A represents an oxygen or sulphur atom,
Z represents an oxygen atom or a hydroxyimino group,
X represents a hydrogen or halogen atom,
the dotted lines represent bonds which may be unsaturated or saturated,
each of $R_1$ and $R_2$, which may be the same or different, represents a hydrogen atom or an alkyl group, and
$R_3$ represents a hydrogen or halogen atom, or a methyl group, and
$R_4$ represents a hydrogen atom, or
$R_3$ and $R_4$ together with the two carbon atoms to which they are attached represent a benzene ring, and their salts with pharmaceutically acceptable bases, in particular their physiologically acceptable alkali metal and amine salts.

Preferably in formula I n represents 0 and $R_1$ and $R_2$ both represent hydrogen atoms.

$R_3$ and $R_4$ preferably both represent hydrogen atoms.

Both the dotted lines in formula I represent unsaturated bonds such that the X group is carried on a naphthalene nucleus in preferred compounds.

The compounds of the formula I, wherein Z represents an oxygen atom, may be prepared by reaction of a compound of the formula II

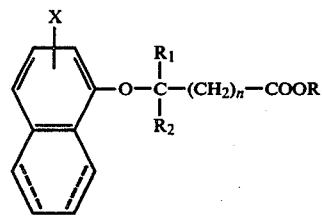

(II)

(wherein R represents a hydrogen atom or an alkyl group and the other symbols are as defined for formula I) with a heteroaryl acid chloride or anhydride which corresponds to one of the formulae IIIa and IIIb

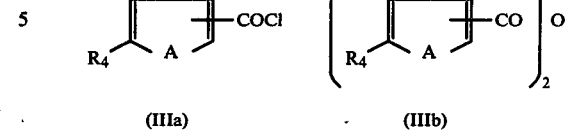

(in which A, $R_3$ and $R_4$ are as defined for formula I) under the conditions of a FRIEDEL-CRAFTS reaction, i.e. in the presence of a Lewis acid, such as AlCl$_3$, and in one of the solvents conventionally used for FRIEDEL-CRAFTS reactions such as methylene chloride, dichloroethane, benzene or carbon disulphide, at a temperature between −20° C. and the reflux temperature of the solvent, and, when R represents an alkyl group, following this reaction by hydrolysis of the ester obtained, preferably with a base in alcoholic or aqueous alcoholic medium.

The oximes of the formula I (i.e. Z=hydroxyimino) may be prepared by reaction of hydroxylamine or a mineral acid salt thereof with a ketone of the formula I (i.e. Z=oxygen) suitably in solution in an aqueous or non-aqueous alcohol, in the presence of a base such as an alkali metal or alkaline earth metal hydroxide or carbonate or in a solution of pyridine.

The salts may be prepared by reaction of the acid with a pharmaceutically acceptable base e.g. with an alkaline metal hydroxide or a pharmaceutically acceptable amine in the solvents commonly used for salifications, for example an alcohol, a ketone, etc.

The invention also provides a pharmaceutical composition which comprises, as active ingredient, a compound of the formula I or a pharmaceutically acceptable salt thereof together with a pharmaceutically acceptable vehicle.

The invention further provides a method of treating a patient which method comprises administering to the patient a compound of the formula I or a pharmaceutically acceptable salt thereof.

The following Examples illustrate the invention. The compounds given are characterized by their melting point; they have been subjected to analytical study (elementary analysis, potentiometric titrations, IR and NMR spectra) which confirm the formulae given.

EXAMPLE 1

[4-(2-Thenoyl)-1-naphthyloxy]-acetic acid (a) Ethyl (1-naphthyloxy)-acetate 432 g 1-naphthol, 602 g ethyl 2-bromoacetate, 276 g potassium carbonate and 2.160 l. ethanol are refluxed for 18 hours, the precipitate filtered, the solvent evaporated under reduced pressure and the residue recrystallized from petroleum ether. The ester, which melts at 52° C., is obtained with an 80% yield.

(b) Ethyl [4-(2-thenoyl)-1-naphthyloxy]-acetate 483 g ethyl 1-naphthyloxyacetate and 308 g thiophene-2-carboxylic acid chloride was dissolved in 3.570 l. methylene chloride. While the mixture is being maintained at about −10° C., 291 g aluminium chloride are introduced slowly; after 2 hours at −10° C., the mixture is brought back to 25° C. and the stirring maintained for 12 hours. The mixture is then poured into 2 Kg iced water, the organic phase decanted off, washed with dilute aqueous sodium hydroxide solution then water and the solvent evaporated. 562 g of the ester are thus obtained. After recrystallisation from isopropyl ether, it melts at 79° C.

(c) [4-(2-Thanoyl)-1-naphthyloxy]-acetic acid

A solution of 340 g of the ester obtained according to (b) and 80 g sodium hydroxide in 1.3l. 75% aqueous ethanol is maintained at reflux for 20 minutes. 1 l. water is added, the alcohol removed and the mixture acidified by the addition of 10% hydrochloric acid. The acid is extracted in ethyl ether. After evaporation of the solvent, 270 g recrystallisable with an 85% yield from acetone or isopropyl ether are obtained.

Melting Point = 164° C.

This acid may also be prepared by reaction of thiophene-2-carboxylic acid chloride with 1-naphthyloxyacetic acid using the same preparational method as described in (b); the yields for this reaction are however lower.

The potassium salt of this acid, prepared by reaction of an equivalent of potassium hydroxide with the acid in solution in methanol, forms a hydrate which melts above 300° C.

The tri(hydroxymethyl)methylamine salt, particularly useful because of its solubility in aqueous medium, is prepared by reaction of an equivalent of the amine with the acid in solution in 2-butanone. After recrystallisation from ethanol, it melts at 160° C.

EXAMPLE 2

[4-(2-Thienyl-hydroxyiminomethyl)-1-naphthyloxy]-acetic acid 5 g [4-(2-thenoyl)-1-naphthyloxy]-acetic acid are dissolved in 50 ml pyridine. 1.5 g hydroxylamine hydrochloride are introduced in solution and the mixture maintained at reflux temperature for 12 hours. The solvent is then removed under reduced pressure, the residue washed with a dilute aqueous hydrochloric acid solution; the oxime obtained with a 95% yield, which is a mixture of two stereoisomers, melts at 215° C.

EXAMPLE 3

[4-(3-Furoyl)-1-naphthlyloxy]-acetic acid (a) To a solution of 26.2 g ethyl-1-naphthyloxyacetate in 260 ml methylene chloride maintained at 0° C., there are introduced 15 g furan-3-carboxylic acid chloride and then, little by little, 15.2 g aluminium chloride. After 2 hours at 0° C., the mixture is held at 40° C. for 8 hours. The mixture is then poured into a ice/concentrated hydrochloric acid mixture. The final product is extracted in ethyl ether and the recrystallised from ethanol. There are thus obtained 31.4 g ethyl [4-(3-furoyl)-1-naphthyloxy]-acetate which melts at 103° C.

(b) Hydrolysis 15 g of the ester obtained according to (a) are dissolved in 300 ml ethanol; after addition of 7.6 g potassium carbonate in solution in 25 ml water, the mixture is refluxed for 17 hours and the alcohol removed under reduced pressure. The residue is purified by dissolution in water; the final product is extracted from the aqueous phase after acidification. 12 g of the acid which, after recrystallisation from dichloroethane, melts at 177° C. are obtained.

EXAMPLE 4

[4-(2-Thenoyl)-5,6,7,8-tetrahyro-1-naphthyloxy]-acetic acid (a) Methyl (5,6,7,8-tetrahyro-1-naphthyloxy)-acetate 10 g 5,6,7,8-tetrahyro-1-naphthol are dissolved in 150 ml 2-butanone and then 18.5 g potassium carbonate and 12.3 g methyl bromoacetate are introduced into the mixture. After having been refluxed for 24 hours, the mixture is filtered, the solvent evaporated under reduced pressure and after removal of the starting phenol soluble in aqueous basic medium, 13.1 g of final product are distilled.

B. $Pt_{0.05} = 105°$ C.

(b) Methyl [4-(2-thenoyl)-5,6,7,8-tetrahydro-1-naphthyloxy]-acetate

To a solution maintained at 0° C. of 12.5 g of the ester obtained according to (a) and 8.79 g thiophene-2-carboxylic acid chloride in 130 ml methylene chloride, there are added little by little 7.9 g aluminium chloride. The mixture is then maintained at reflux temperature for 6 hours and then poured into a mixture of ice and hydrochloric acid. The final product is recrystallised from methanol. There are obtained, with an 85% yield, 16.35 g of the ester which melts at 85° C.

(c) Hydrolysis 9 g of the ester according to (b) are dissolved in 100 ml aqueous ethanol. 1.8 g potassium hydroxide dissolved in 25 ml water are added and the mixture refluxed for 8 hours. The ethanol is evaporated and the remaining aqueous phase acidified by addition of mineral acid. The acid is extracted in ethyl ether.

After recrystallisation from benzene, 7.7 g of the acid, which melts at 121° C., are obtained.

In the following Table I there are given the structural formulae of a certain number of compounds which have been prepared using the operational methods described above and these are given by way of illustration of the invention.

TABLE I

| Example No. | Structural Formulae | M. Pt. (°C.) |
|---|---|---|
| 1 | [structure: 2-thienyl-C(=O)-naphthyl-O-CH₂-COOH] | 164 |

TABLE I-continued

| Example No. | Structural Formulae | M. Pt. (°C.) |
|---|---|---|
| 2 | thiophene-C(=NOH)-naphthalene-O-CH₂-COOH | 215 |
| 3 | furan-C(=O)-naphthalene-O-CH₂-COOH | 177 |
| 4 | thiophene-C(=O)-(tetrahydronaphthalene)-O-CH₂-COOH | 121 |
| 5 | furan-C(=O)-(tetrahydronaphthalene)-O-CH₂-COOH | 161 |
| 6 | thiophene-C(=O)-naphthalene(Br)-O-CH₂-COOH | 166 |
| 7 | (5-CH₃-thiophene)-C(=O)-naphthalene-O-CH₂-COOH | 172 |
| 8 | (5-CH₃-thiophene)-C(=NOH)-naphthalene-O-CH₂-COOH | 182 (hemihydrate) |
| 9 | furan-C(=O)-naphthalene-O-CH₂-COOH | 170 |

TABLE I-continued

| Example No. | Structural Formulae | M. Pt. (°C.) |
|---|---|---|
| 10 | 2-thienyl-CO-(naphthalene)-O-CH₂-COOH | 178 |
| 11 | 2-furyl-C(=NOH)-(naphthalene)-O-CH₂-COOH | 196 |
| 12 | benzofuran-2-yl-CO-(naphthalene)-O-CH₂-COOH | 240 |
| 13 | 2-thienyl-CO-(naphthalene)-O-(CH₂)₂-COOH | 125 |
| 14 | 2-furyl-CO-(naphthalene)-O-(CH₂)₂-COOH | 155 |
| 15 | 2-furyl-CO-(naphthalene)-O-(CH₂)₂-COOH | — |
| 16 | 2-thienyl-CO-(naphthalene)-O-(CH₂)₃-COOH | 144 |
| 17 | 2-furyl-CO-(naphthalene)-O-(CH₂)₃-COOH | 130 |

TABLE I-continued

| Example No. | Structural Formulae | M. Pt. (°C.) |
|---|---|---|
| 18 | [thiophene-CO-naphthyl-O-CH(CH₃)-COOH] | 170 |
| 19 | [furan-CO-naphthyl-O-CH(CH₃)-COOH] | 177 |
| 20 | [thiophene-CO-naphthyl-O-C(CH₃)₂-COOH] | 135 |
| 21 | [thiophene-C(=NOH)-naphthyl-O-C(CH₃)₂-COOH] | 204 |

The compounds according to the invention show in animals a uricosuric activity; a certain number also have a very valuable diuretic and saluretic activity. These properties have been shown by way of pharmacological tests, the methods and results of which are given below:

The acute toxicity of the new compounds has been studied in mice orally, according to the method of BLISS (Quart. J. Pharm. Pharmacol. (1938) 2 192–216); with the exception of the compounds in Examples 3 and 13, which have an $LD_{50}$ in the region of 700 mg/kg, all the other compounds have an $LD_{50}$ above 1000 mg/kg.

The uricosuric activity of the compounds has been shown by the method described by H. C. SCARBOROUGH and G. R. McKINNEY (J. Med. Pharm. Chem. (1962) 5 175) as well as by E. KREPPEL (Med. Exptl. (1959) 1 285); phenol red is administered intravenously to rats and the development of the concentration of this colourant in their blood is studied as a function of time. It is known that rats, which one hour before the beginning of the experiment have received an uricosuric agent, show, in comparison with non-treated animals, retention of phenol red in the blood.

All the compounds according to the invention tested cause retention of phenol red; for each, the minimum statistically active dose is always less than 1/10 of the $LD_{50}$. In Table II are shown the results obtained with some representative compounds, as well as for 2-ethyl-3-(4-hydroxy-3,5-diiodobenzoyl)-benzo[b]furane, or benziodarone, an uricosuric used in human therapy and of which the $LD_{50}$ determined as above is 1400 mg/kg. The ratio is that of the concentrations of phenol red found in the blood of animals which have received the test compounds at the dose indicated at the specified time to the concentrations for non-treated animals.

TABLE II

| Compound of Example No. | Dose (mg/kg) | Maximum Ratio measured (%) | Time of measurement after injection of the colourant (in minutes) |
|---|---|---|---|
| 1 | 100 | 121 | 60 |
|  | 50 | 100 | 45 |
| 2 | 100 | 77 | 45 |
| 6 | 50 | 116 | 60 |
| 7 | 100 | 44 | 15 |
| 10 | 100 | 53 | 30 |
| 12 | 50 | 51 | 15 |
| 14 | 75 | 80 | 60 |
| benzio-darone | 100 | 53 | 45 |

The diuretic ability of the novel compounds according to the invention has been studied in mice. It is expressed in Table III in the form of a ratio of the volume of urine for the treated animals received during 2 and 4 hours after administration (at the indicated dose) of the test compound to the volume measured under the same conditions for the control animals.

TABLE III

| Compound of Example No. | Dose mg/kg (p.o.) | Diuretic Ability | |
|---|---|---|---|
|  |  | 0 to 2 hours | 0 to 4 hours |
| 3 | 50 | 1.48 | 1.44 |
|  | 20 | 1.53 | 1.31 |
| 7 | 50 | 2.01 | 1.70 |
| 10 | 200 | 1.38 | 1.77 |

The new compounds of the present invention may be used in the treatment of pathologic hyperuricemia or that provoked by certain medications or in a treatment of affectations characterised, in particular, by an excessive retention of fluid and electrolytes in the organism notably in gout, oedematous states and hypertension.

The compounds may be administered, alone or in combination, associated with pharmaceutically acceptable vehicles, by injection, by oral administration in the form of capsules or tablets, and at doses which, depending on the nature and extent of the symptoms to be treated, may be from 50 mg to 1 g.

We claim:

1. A compound of the general formula I

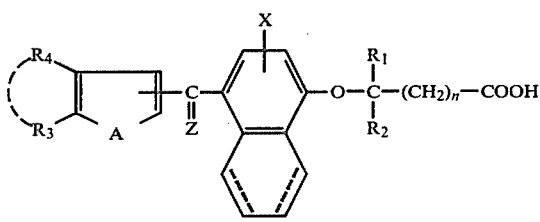

wherein
n represents 0, 1 or 2,
A represents an oxygen or sulphur atom,
Z represents an oxygen atom or a hydroxyimino group,
X represents a hydrogen or halogen atom,
the dotted lines represent bonds which may be unsaturated or saturated,
each of $R_1$ and $R_2$, which may be the same or different, represents a hydrogen atom or an alkyl group, and
$R_3$ represents a hydrogen or halogen atom, or a methyl group, and
$R_4$ represents a hydrogen atom, or
$R_3$ and $R_4$ together with the two carbon atoms to which they are attached represent a benzene ring, or a salt thereof with a pharmaceutically acceptable base.

2. A compound according to claim 1 wherein n represents 0, and $R_1$ and $R_2$ both represent hydrogen atoms.

3. A compound according to claim 1 wherein $R_3$ and $R_4$ both represent hydrogen atoms.

4. A compound according to claim 1 wherein both the dotted lines represent unsaturated bonds.

5. A compound according to claim 1 which is [4-(2-thenoyl)-1-naphthyloxy]-acetic acid or a salt thereof with a pharmaceutically acceptable base.

6. A compound according to claim 1 which is [4-(3-thenoyl)-1-naphthyloxy]-acetic acid or a salt thereof with a pharmaceutically acceptable base.

7. A compound according to claim 1 which is [4-(3-furoyl)-1-naphthyloxy]-acetic acid or a salt thereof with a pharmaceutically acceptable base.

8. A pharmaceutical composition which composition comprises, as active ingredient, a compound of the general formula I

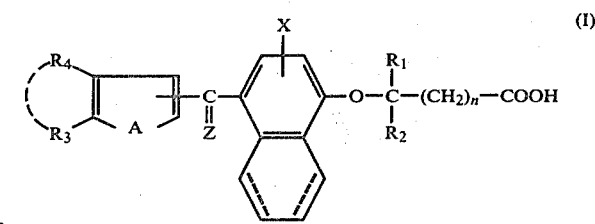

wherein
n represents 0, 1 and 2,
A represents an oxygen or sulphur atom,
Z represents an oxygen atom or a hydroxyimino group,
X represents a hydrogen or halogen atom,
the dotted lines represent bonds which may be unsaturated and saturated,
each of $R_1$ and $R_2$, which may be the same or different, represents a hydrogen atom or an alkyl group, and
$R_3$ represents a hydrogen or halogen atom, or a methyl group, and
$R_4$ represents a hydrogen atom, or
$R_3$ and $R_4$ together with the two carbon atoms to which they are attached represent a benzene ring, or a salt thereof with a pharmaceutically acceptable base together with a pharmaceutically acceptable vehicle.

9. A composition according to claim 8 wherein the active ingredient is selected from the group consisting of
[4-(2-thenoyl)-1-naphthyloxy]-acetic acid and salts thereof with pharmaceutically acceptable bases,
4-[3-thenoyl)-1-naphthyloxy]-acetic acid and salts thereof with pharmaceutically acceptable bases, and
[4-(3-furoyl)-1-naphthyloxy]-acetic acid and salts thereof with pharmaceutically acceptable bases.

10. A method of treating a patient suffering from hyperuricemia which comprises administering to said patient a compound of the formula I:

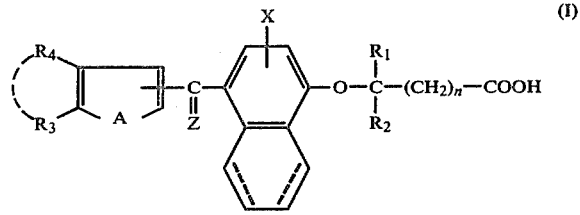

wherein
n represents 0, 1 or 2,
A represents an oxygen or sulphur atom,
Z represents an oxygen atom or a hydroxyimino group,
X represents a hydrogen or halogen atom,
the dotted lines represent bonds which may be unsaturated or saturated,
each of $R_1$ and $R_2$, which may be the same or different, represents a hydrogen atom or an alkyl group, and
$R_3$ represents a hydrogen or halogen atom, or a methyl group, and
$R_4$ represents a hydrogen atom, or
$R_3$ and $R_4$ together with the two carbon atoms to which they are attached represent benzene ring, or a pharmaceutically acceptable salt thereof, said compound being administered in an amount effective to provide an anti-hyperuricemia effect.

* * * * *